US00PP16570P3

(12) United States Plant Patent
Herman et al.

(10) Patent No.: US PP16,570 P3
(45) Date of Patent: May 23, 2006

(54) PEKIN LILAC TREE NAMED 'SUNDAK'

(50) Latin Name: *Syringa pekinensis*
Varietal Denomination: SunDak

(75) Inventors: Dale E. Herman, Fargo, ND (US); Scott C. Redlin, Cary, NC (US); Larry J. Chaput, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 141 days.

(21) Appl. No.: 10/804,526

(22) Filed: Mar. 18, 2004

(65) Prior Publication Data

US 2005/0210555 P1 Sep. 22, 2005

(51) Int. Cl.
*A01H 5/00* (2006.01)

(52) U.S. Cl. ..... Plt./248
(58) Field of Classification Search ..... Plt./248
See application file for complete search history.

(56) References Cited

PUBLICATIONS

North Dakota Nursery News [online]. vol. 5, Issue 1, Jan. 24, 2001 [retrieved on Aug. 18, 2004]. Retrieved from the Internet: <http://www.agdepartment.com/Programs/pp/ND-NursNeews2001.pdf>.*

2002 Annual Highlights Agriculture at North Dakota State University [online] [retrieved on Aug. 18, 2004]. Retrieved from the Internet: <http://www.ag.ndsu.nodak.edu/legisLa-tors/highlights/02page0.1htm>.*

* cited by examiner

*Primary Examiner*—Anne Marie Grunberg
*Assistant Examiner*—June Hwu
(74) *Attorney, Agent, or Firm*—Jondle & Associates P.C.

(57) ABSTRACT

'SunDak' is a new cultivar of *Syringa pekinensis,* Pekin lilac tree. This new cultivar has a coppery-orange exfoliating bark pattern that separates into shaggy curls; large, abundantly produced creamy-white flower panicles; attractive seed capsules; upright broadly-oval to rounded form; typically grows multiple-trunked and with improved winter hardiness.

3 Drawing Sheets

Genus and species: *Syringa pekinensis.*
Cultivar denomination: 'SunDak'.

BACKGROUND OF THE INVENTION

The present invention comprises a new and distinct cultivar of Pekin lilac tree, botanically known as *Syringa pekinensis,* and hereinafter referred to by the cultivar name 'SunDak'. 'SunDak' is a product of a planned tree selection program which had the objective of creating a new cultivar of Pekin lilac tree having striking coppery-bronze exfoliating bark pattern, improved winter hardiness and various aesthetic qualities as listed in the Detailed Description of the Plant.

In 1980, bulk seed was collected from a hardy parental tree growing on the North Dakota State University (NDSU) campus. Several seedling plants from the above seed collection were planted on the NDSU campus on May 16, 1983. The new cultivar is a seedling selection from this seedling population. The selection possessed the qualities as outlined above and listed below in the DETAILED DESCRIPTION OF THE NEW PLANT.

The first act of asexual reproduction of 'SunDak' was accomplished by grafting onto *Syringa pekinensis* rootstocks by applicant from the initial selection of Feb. 8, 1996 in a controlled environment at NDSU, Fargo, North Dakota. Horticultural examination of selected units initiated on Jun. 29, 1999 has demonstrated that the combination of characteristics as herein disclosed for 'SunDak' are firmly fixed and are retained through successive generations of asexual reproduction.

'SunDak' has not been observed under all possible environmental conditions. The phenotype may vary with variations in environment such as temperature, light intensity, and day length. The following observations, measurements and comparisons describe the plant grown on the NDSU campus or plants grown under greenhouse/field conditions, which approximate those generally used in commercial practices.

DESCRIPTION OF DRAWINGS

This new lilac tree is illustrated by the accompanying photographs which show the entire tree, close-up of the flower panicles, trunk, close-up of the trunk showing exfoliating bark patterns and a close-up of the seed clusters (capsules). The colors shown are as true as can be reasonably obtained by conventional photographic procedures.

DETAILED DESCRIPTION OF THE NEW PLANT

Figure 1:
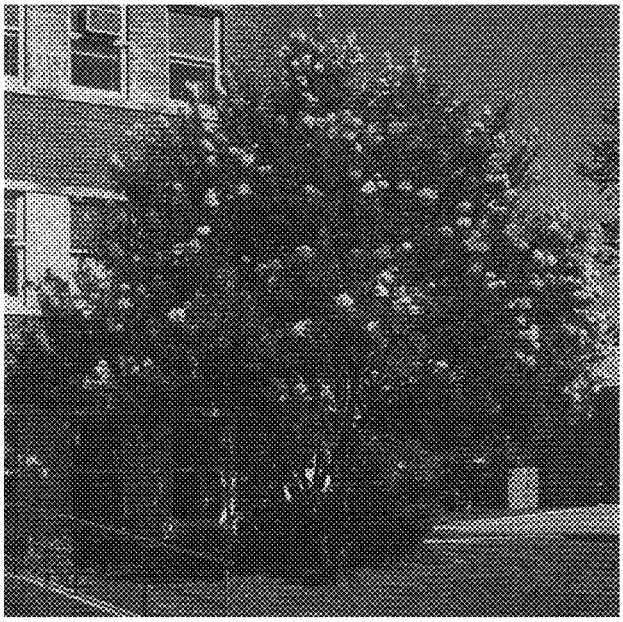
FIG. 1 shows the complete tree in dense foliage.
Figure 2:
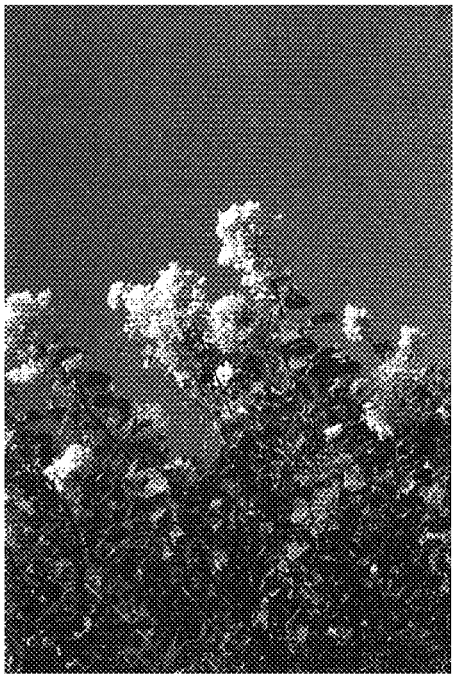
FIG. 2 is a close-up of the dense foliage with flower panicles.
Figure 3:
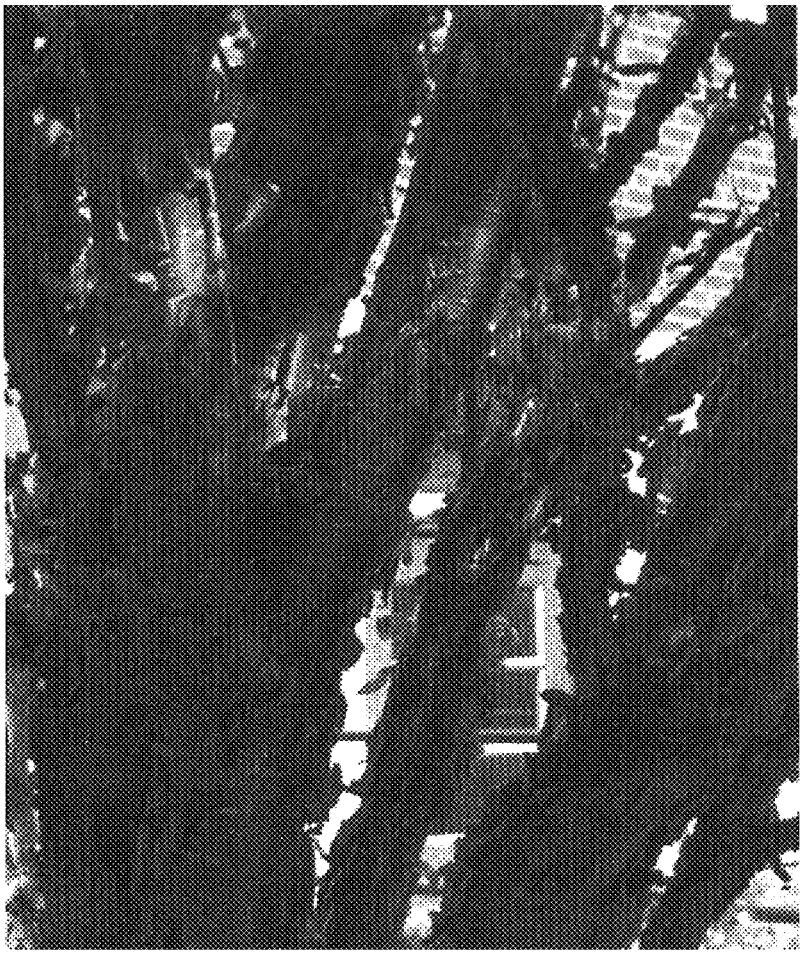
FIG. 3 shows the trunk.
Figure 4:
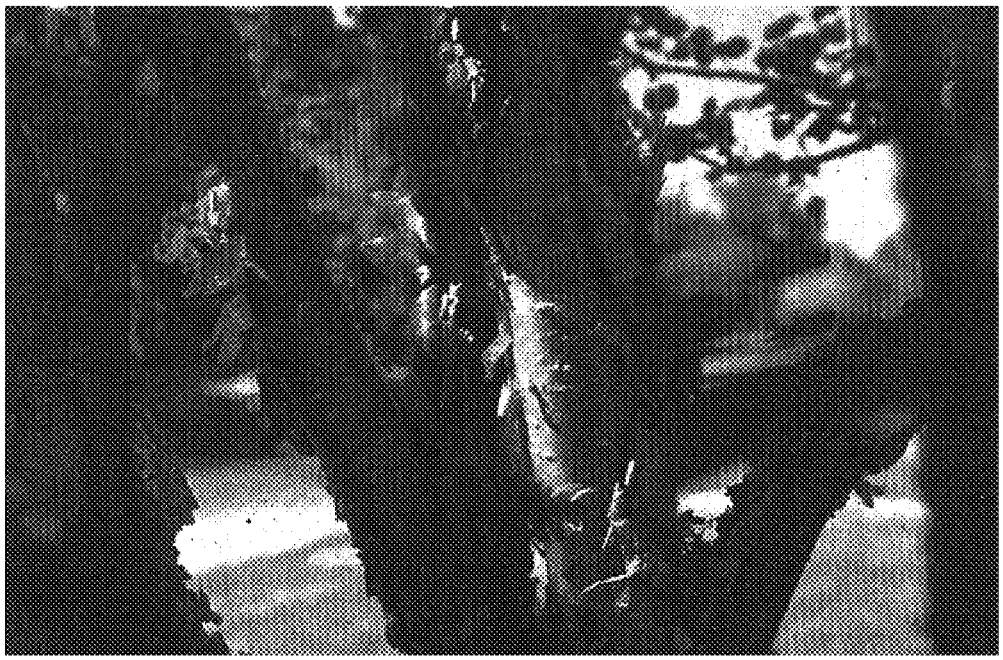
FIG. 4 is a close-up of the trunk showing exfoliating bark patterns.
Figure 5:
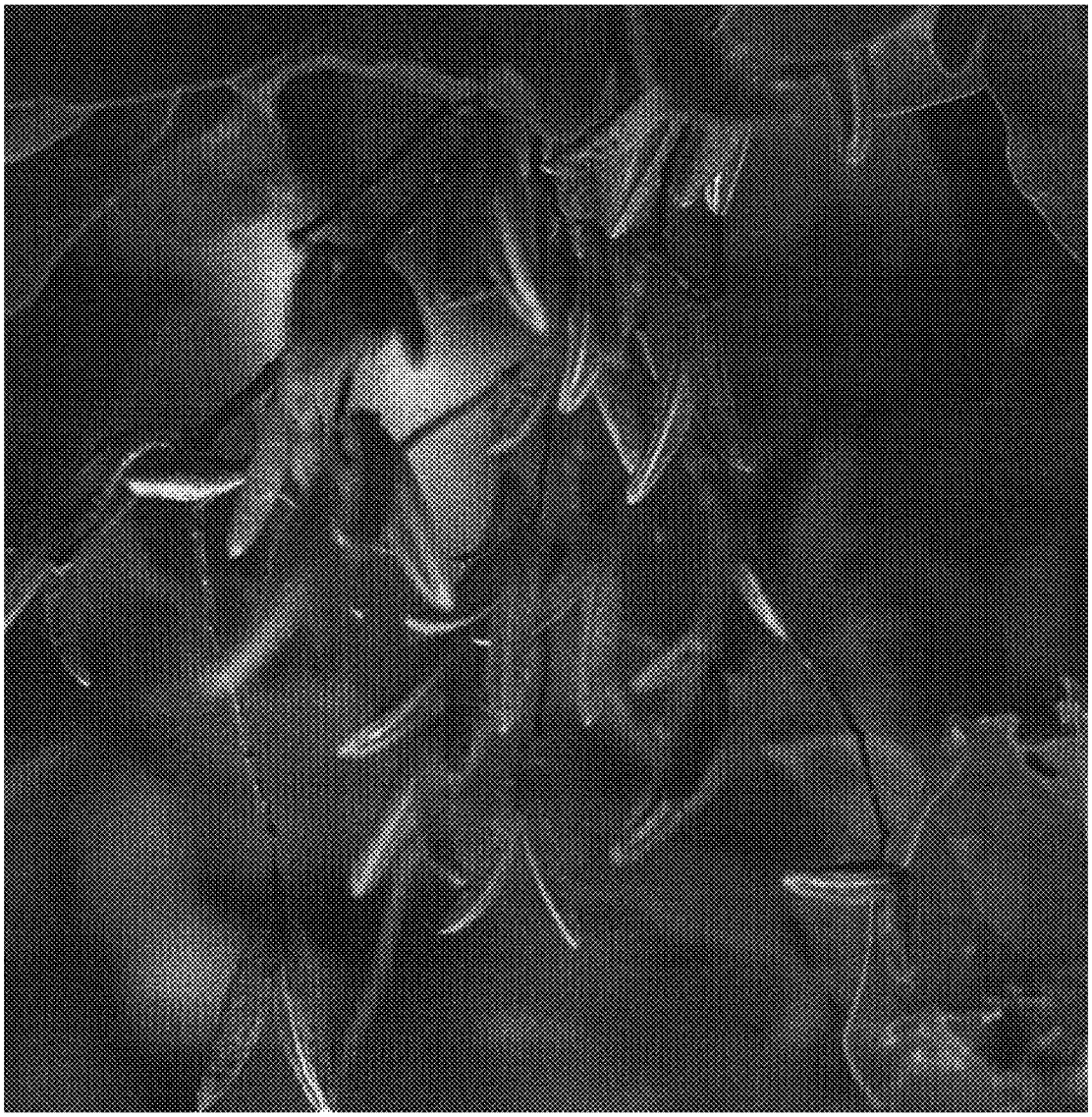
FIG. 5 is a close-up of the seed clusters (capsules).

The following traits and characteristics. describe the new cultivar. Color references are to The R.H.S Colour Chart of The Royal Horticultural Society of London (R.H.S.).

Classification:
Origin: This species is native to China. Seedlings were grown from seed collected from a hardy tree growing for over 50 years on the NDSU campus. The origin or source of the original tree is unknown. 'SunDak' was selected from several seedlings of this population planted on the NDSU campus in 1983.
Parentage:
*Seed parent.*—*Syringa pekinensis*— Pekin Lilac.
*Pollen parent.*—*Syringa pekinensis*— Pekin Lilac.
Species: *Syringa pekinensis.*
Common name: Pekin Lilac.
Commercial name: Copper Curls™ Pekin Lilac.
Trunk:
Multiple stem: Two main trunks forming clump.
Size: At 21 years old, average diameter of two trunks, 19.1 cm.
Bark: Coppery-orange (ranges from RHS 164A to 165B), average length of exfoliating sheets 3.6 cm.
Height: At 21 years old=8.1 m; width=6.2 m.
Growth habit or form: Upright, broadly oval to rounded.
Growth rate: 34 cm per year under sod conditions.
Trunk lenticels:
Length: Average=8 mm on a turn of 9 cm diameter.
Shape: Torpedo-like.
Texture: Slightly raised from the bark with a rough texture.
Color: Greyed-orange (RHS 165D).
Quantity—150 lenticels/30 cm of trunk length on 9 cm diameter trunk.
Branches:
Angle of attachment: Average angle of 13 branched pairs=33.0°.
Spacing: Variable.
Size: Crown diameter of tree, 6.2 m; height=8.1 m.
Surface texture: Smooth.
Bark: Coppery-orange (RHS 164A to 165B).
Branches lenticels:
Size: Average=3 mm on branches having a 3 cm diameter.
Shape: Torpedo-like.
Texture: Slightly raised from the bark with a rough texture.
Color: Greyed-orange (RHS 165D).
Foliage:
Size of leaf:
*Length.*—Range 4.0–7.6 cm, average 6.1 cm.
*Width.*—Range 2.4–7.3 cm, average 4.1 cm.
Shape of leaf: Ovate to ovate-lanceolate.
Margin: Entire.
Texture: Medium.
Pubescence distribution: None (glabrous).
Color: Upper side, Green (ranges from RHS 137A to 137B).
Petiole:
*Length.*—Ranges from 8 to 30 mm; average=18 mm.
*Diameter.*—1 mm.
*Surface texture.*—Smooth.
*Color.*—Olive green (RHS 152C).
Ribs and veins: Scarcely veined.
Thorns and spines: None.
Buds: Variably ovate.
*Size.*—Length averages 4.2 mm; width averages 3.0 mm.
*Scales.*—12 scales per bud.
*Color.*—Ranges from RHS Greyed Orange Group 164A to 164B.
*Leaf scar*—Cresent-shaped.
Flower (florets):
Flower type: Tubular, 4-lobed, borne in large panicles.
Length: 0.4–0.5 cm; average=0.45 cm.
Width: 0.5–0.7 cm; average=0.58 cm.
Petal:
*Number.*—One, but tubular, flaring horizontally to 4 lobes.
*Lobe length.*—0.25–0.35 cm; average=0.29 cm.
*Lobe width.*—0.15–0.22 cm; average=0.18 cm.
Color: Creamy-white (RHS White Group 155D).
Shape: Oblong-conical to pyramidal to nearly globose panicle containing many florets.
Size:
*Length.*—Range of 10.2 cm to 23.4 cm; average=15.6 cm.
*Width.*—Range of 10.2 cm to 23.4 cm; average=16.7 cm.
Calyx:
*Shape.*—Campanulate (bell-like, cylindrical) with 4 tiny lobes at tip observed under binocular dissecting scope, but insignificant to the naked eye.
*Length.*—0.15 cm.
*Width.*—0.10 cm.
*Color.*—RHS 155D (White).
Length of flowering (bloom period): 15–20 days, depending on the temperature; flowers last longer under cool temperatures.
Lastingness of flowers on the plant: 5–7 days, but varies with temperature; individual florets open from the bottom of the panicle to the top of the panicle.
Fragrance: Very aromatic and similar to *Ligustrum* (Privet).
Reproductive parts;
Stamen:
*Number.*—Two.
*Filament.*—Length — 0.4–0.5 cm; average=0.45 cm. Width — 0.05 cm. Color — RHS 155D (White).
*Anther.*—Length — 0.2–0.225 cm, average=0.22 cm. Width — 0.125 cm. Color — RHS 158C (yellow-white) to RHS 160B (greyed-yellow) to RHS 164B (greyed-orange) to RHS 164A (color darkens in this sequence as anthers age from day 1 to day 4 of flower age).
Pistil:
*Number.*—One.
*Length.*—0.2–0.25 cm; average=0.225 cm.
*Width.*—0.025 cm.
*Stigma.*—Length — 0.005–0.1 cm; average=0.085 cm. Width — 0.035 cm. Color — RHS 155D (White).
*Style.*—Length— 0.14 cm. Width — 0.025 cm. Color — RHS 155D (White).
Fruit:
Shape: Oblong-conical to pyramidal to nearly globose, containing many capsules.
Texture of capsule Slightly rough due to the presence of numerous tiny lenticel-like protuberances dotting the entire surface of the capsule.
Size:
*Length.*—Range from 9.0 cm to 22.2 cm; average=14.4 cm.
*Width.*—Range of 9.0 cm to 22.2 cm; average=15.5 cm.
Fruit structure:—Two-celled oblong capsule.
*Size.*—Range of 14 to 20 mm; average=17 mm long.
*Color.*—Ranges from RHS Greyed Orange Group 164B to 165C.
Seed:
Size:
*Length.*—Range of 13 to 16 mm; average=14.8 mm.
*Width.*—Range of 4 to 7 mm; average=6.0 mm.

Insect and disease resistance: No apparent disease or insect problems to date.

COMPARISON WITH MOST SIMILAR CULTIVAR

'Sundak' is different from its parents in having very bright coppery-orange bark that exfoliates dramatically. It is cold hardy to USDA zone 3 to which its parents are not.

Of the commercial lilac trees known to the applicant, the most similar in comparison to 'SunDak' are the cultivars *Syringa pekinensis* 'Morton'—China Snow® and *Syringa pekinensis* 'DTR 124'—Summer Charm® (U.S. Plant Pat. No. 8,951). China Snow® is characterized by upright, rounded form with cherry-like, amber-colored, exfoliating bark. Summer Charm® is reputed to be a small, spreading tree with attractive smooth bark, and dark green, lustrous foliage with no mention of exfoliating bark. Compared to these two cultivars, 'SunDak' has a number of important attributes such as:

1) Striking, distinctly coppery-orange exfoliating bark pattern; the bark with its attractive sheen tends to peel and separate in shaggy curls;
2) Large, attractive, abundantly-produced, creamy-white flower panicles;
3) Attractive seed clusters (capsules) which change from green to tannish-brown and cling to the branches for added winter effect;
4) Upright, broadly oval to rounded form;
5) Typically grows multiple-trunked; and
6) Improved winter hardiness (−34° to −37° C.).

What is claimed is:

1. A new and distinct *Syringa pekinensis* (Pekin lilac) tree as shown and described herein.

* * * * *